US007431887B2

United States Patent
Storek et al.

(10) Patent No.: US 7,431,887 B2
(45) Date of Patent: Oct. 7, 2008

(54) MICROFLUIDIC DEVICE AND METHOD WITH TRAPPING OF SAMPLE IN CAVITIES HAVING LIDS THAT CAN BE OPENED OR CLOSED

(76) Inventors: David Storek, Golvläggaregatan 4 C, S-412 62 Göteborg (SE); Niklaus Schneeberger, Route des Buchilles 42, CH-2017 Boudry (CH); Britta Ottosson, Dalgángsgatan 28, S-431 39 Mölndal (SE); Anafol Krozer, Klamparegatan 5, S-413 17 Göteborg (SE); Robert P Otillar, Jr., 833 Ashbury #2, San Francisco, CA (US) 94117-4465

( * ) Notice: Subject to any disclaimer, the term of this patent is extended or adjusted under 35 U.S.C. 154(b) by 116 days.

(21) Appl. No.: 10/248,847

(22) Filed: Feb. 24, 2003

(65) Prior Publication Data

US 2004/0132170 A1 Jul. 8, 2004

Related U.S. Application Data

(63) Continuation of application No. PCT/SE01/01798, filed on Aug. 23, 2001, now abandoned.

(60) Provisional application No. 60/228,015, filed on Aug. 24, 2000.

(51) Int. Cl.
  *G01N 33/00* (2006.01)
(52) U.S. Cl. .......................... 422/99; 422/102; 436/149; 436/174; 436/526; 435/305.3

(58) Field of Classification Search .................. 422/99, 422/102; 436/174, 149, 526; 435/305.3
See application file for complete search history.

(56) References Cited

U.S. PATENT DOCUMENTS

| 4,414,243 | A |   | 11/1983 | Cline |
|-----------|---|---|---------|-------|
| 4,822,566 | A |   | 4/1989  | Newman |
| 4,932,255 | A |   | 6/1990  | Brace et al. |
| 5,235,235 | A |   | 8/1993  | Martin et al. |
| 5,468,809 | A |   | 11/1995 | Ghisellini et al. |
| 5,655,665 | A |   | 8/1997  | Allen et al. |
| 5,755,942 | A | * | 5/1998  | Zanzucchi et al. .......... 204/454 |
| 5,814,525 | A |   | 9/1998  | Renschler et al. |
| 5,869,748 | A |   | 2/1999  | Stevenson et al. |
| 5,874,219 | A |   | 2/1999  | Rava et al. |
| 5,922,537 | A |   | 7/1999  | Ewart et al. |

(Continued)

FOREIGN PATENT DOCUMENTS

FR  2781886  2/2000

(Continued)

OTHER PUBLICATIONS

Barnes-Svarney, Patricia, Ed., The New York Public Library Science Desk Reference (MacMillan USA 1995), p. 294.*

*Primary Examiner*—Jill Warden

(57) ABSTRACT

System and method for providing a sample preparing arrangement (10) submergible in a liquid medium that includes a carrier structure (11) having at least one cavity (12) therein and that is in communication with an arrangement (13) for controllable generation of a magnetic field through influence of a control signal. The sample preparing arrangement includes a magnetic covering structure (14) for covering and/or uncovering the cavity in operative interaction with the magnetic field.

33 Claims, 3 Drawing Sheets

U.S. PATENT DOCUMENTS

| | | |
|---|---|---|
| 5,922,617 A | 7/1999 | Wang et al. |
| 5,976,466 A | 11/1999 | Ratner et al. |
| 5,981,297 A | 11/1999 | Baselt |
| 6,161,437 A | 12/2000 | Brennan et al. |
| 6,358,752 B1 | 3/2002 | Durst et al. |
| 6,468,810 B1 | 10/2002 | Korpela |
| 6,572,830 B1 * | 6/2003 | Burdon et al. ......... 422/186.29 |
| 6,630,359 B1 | 10/2003 | Caillat et al. |
| 2002/0001855 A1 | 1/2002 | Prentiss et al. |
| 2002/0086443 A1 | 7/2002 | Bamdad |
| 2002/0119470 A1 | 8/2002 | Nerenberg et al. |
| 2005/0148101 A1 | 7/2005 | Bamdad et al. |

FOREIGN PATENT DOCUMENTS

| | | |
|---|---|---|
| WO | WO 9615450 A1 | 5/1996 |
| WO | WO 0043534 A1 | 7/2000 |
| WO | WO 00/49382 | 8/2000 |
| WO | WO 0054882 A1 | 9/2000 |
| WO | WO 0060356 A1 | 10/2000 |

* cited by examiner

MICROFLUIDIC DEVICE AND METHOD WITH TRAPPING OF SAMPLE IN CAVITIES HAVING LIDS THAT CAN BE OPENED OR CLOSED

CROSS REFERENCE TO RELATED APPLICATIONS

This application is a continuation patent application of International Application No. PCT/SE01/01798 filed 23 Aug. 2001 which was published in English pursuant to Article 21(2) of the Patent Cooperation Treaty, and which claims priority to Swedish Application No. 0002990-0 filed 23 Aug. 2000 and to U.S. Provisional Application No. 60/228,015 filed 24 Aug. 2000. Said applications are expressly incorporated herein by reference in their entireties.

BACKGROUND OF INVENTION

1. Technical Field of the Invention

The present invention relates to a method and arrangement for preparing samples submergible in a liquid medium.

2. Background of the Invention

When considering a living organism, for example a human being, an animal or even a plant, a basic subunit of such organisms is a cell. One way to categorize such cells is by the functions they are aimed to perform in an organism; e.g.: epithelial cells, (skin) muscle cells, neural cells and the like. All these cells communicate with the surrounding world via complex mechanisms, which usually involve many different complex molecules called proteins, some of which are embedded into a cell wall. Cells live and die very much like the whole organism; they also grow, divide, and the like. In all these functions, many different parts/components of a given cell take part. These components can be proteins, enzymes (acting as catalysts for certain reactions occurring in the cell) as well as DNAs, RNAs, tRNAs, and the like. Thus, there exists an enormous number of processes (mutations) occurring in an organism per unit time, and also in each cell of the organism. Some of these mutations are important for the cell-well being, but others are dangerous, for instance, cancerous mutations.

Therefore it is very important to be able to foresee, at least partly, the behavior of a cell, to map out the reactions that occur, and their products (usually creation of new cells DNAs and/or proteins). It is equally important to be able to cure maligneous events in the body, which can arise by either invasion of other organisms (viruses or bacterium), or by processes caused within the body itself (autoimmune reactions), or by outside environmental factors such as stress.

In all of these processes, the number of out coming events is immense. Take for example, DNA strands. There are millions upon millions of different DNAs that contribute to production of even larger numbers of proteins whose function and chemistry is far more complex than that of the DNAs themselves.

It would take many lifetimes to establish the structure of even a few thousands of the DNA molecules, not to mention the proteins and/or their functions, or related drugs. Therefore, one needs fast techniques that enable the acquisition of information in parallel, and effective means of storage and handling of such information.

During the past decades, a search to develop such methods has been started. The common name for such techniques has been coined as high throughput screening (HTS). The idea is to prepare, in parallel, fewer samples so as not to use large amounts of expensive and rare chemicals but, to make as many as are feasible, as is possible. The easiest and the most logical (from the information handling point of view o) way is to arrange such complex samples in a matrix. Taken from the semiconductor industry, these matrices are often referred to as "chips".

One example of such preparation is given in FIG. 1, Biophotonics, January/February 2000, Univ. of Wisconsin, Franco Cerrina, et al. According to this technique, a matrix is created by burning away deposits from certain selected places on a chip, while depositing additional chemicals on other places. This method, although fairly fast and cheap, produces a permanent pattern on a matrix which will be used up after a single experiment. Thus, each new experiment requires production of a new matrix.

The number of elements (spots) in a matrix varies depending on the preparation method, but usually does not exceed 10,000; although, matrices as large as including 1,000,000 sites have been reported. The outcome of each single "experiment," therefore, gives at best 10,000 results. In reality this number is much lower (around 20% of best results) due to the very poor quality of even the best matrices produced to date.

FR 2,781,886 concerns fabrication of a microsystem with multiple points for chemical or biological analysis consisting of a structure provided with micro-cups. Each micro-cup is designed to receive a reagent coupled with a conductor polymer. Each micro-cup has a receiving electrode whereon, is fixed, the reagent via of the polymer conductor, with which it is coupled. Each micro-cup also has a counter-electrode arranged so as to apply, in a volume of the micro-cup, an electric field between its counter-electrode and its receiving electrode. The structure has means for simultaneously connecting all the receiving electrodes to a first electric potential and means for simultaneously connecting all the counter-electrodes to a second electric potential for generating said electric field.

U.S. Pat. No. 5,874,219 discloses methods for concurrently processing multiple biological chip assays by providing a biological chip plate comprising a plurality of test wells, each test well having a biological chip having a molecular probe array. Samples are introduced into the test wells; subjecting the biological chip plate to manipulation by a fluid handling device that automatically performs steps to carry out reactions between target molecules in the samples and probes. The biological chip plate is subjected to a biological chip plate reader that interrogates the probe arrays to detect any reactions between target molecules and probes.

U.S. Pat. No. 5,755,942 describes a system for processing a plurality of tests or syntheses in parallel that include a sample channel for moving samples into a micro-laboratory array of a plurality of wells connected by one or more channels for the testing or synthesis of samples. A station is provided for housing the array and an optical system comprising at least one light source and at least one light detector for measuring the samples in the array. A means is provided for electrically connecting the array to an apparatus capable of monitoring and controlling the flow of fluids into the array. Samples are loaded from a common loading channel into the array, and the samples are processed in the wells. Measurements are also taken by the optical system of the samples. The system uses a magnetic valve for opening and closing a channel for micro-fluids.

SUMMARY OF INVENTION

One object of the invention is to present an arrangement which improves the "one by one" experimentation by providing a controllable space.

The technique allows a relatively rapid screening of new chemicals to be used as drugs, both with regard to their function and, importantly, with regard to the determination of the side effects that a given drug might exert. The technique can also be used in many other applications such as genome determination, proteomics and others.

The invention can be used to prepare a ready-to-use-product, which is impossible to modify, but to allow a user for possibility to prepare his or her own "experiment". Thus, one object of the invention is to provide an easy-to-handle platform, which can be used repeatedly and can be prepared in-house. Consequently, the invention is not limited to the surface deposits as is the devices described above (see also FIG. 1), but allows sample preparation either by surface deposition (at the bottom or at the walls of a crater), or by utilizing liquid state reactions allowing reagent contained in the liquid trapped within each well by a cap to mix with reagents contained in the liquid above the craters by opening the "lids" (caps) at will.

In an arrangement configured according to the invention, it is relatively easy to change both the dimensions and the number of the wells. Also, the simplicity of the design will allow integrating the reaction product detection system, on-chip, and perhaps also the facility for multi-well deposition of the active substance.

Another object of the invention is to describe how the detection limits for the events under study can be improved using techniques similar to those used for chip production.

These objects are achieved by the initially mentioned arrangement, which includes a section provided with a device for controllable generation of a magnetic field through influence of a control signal. The magnetic field is generated to trap at least part of the samples. Preferably, the device is a coil or a magnetically active material and it is made of an electrically conducting material, preferably aluminum. In each device, a current of different strength is applied through a conductor whereby the current amplitude and the number of windings in the coil are proportional to the strength of the magnetic field.

According to a first aspect of the invention, the arrangement includes a cavity provided in a substrate and a lid for closing the cavity. Preferably, the lid is a magnetic bead. The bead is directed onto a cavity using external magnets that create magnetic fields counteracting the field created by the material deposited around each cavity. Each cavity is surrounded by a device, which directs the lid using external magnets that create magnetic fields counteracting the field created by material deposited around each cavity. The cavities are etched in a silicon surface and the lid is provided as a large magnetic particle in the liquid. The particle is attracted to a predetermined cavity when the coil of the cavity is energized by electric current to produce magnetic field of spatial attraction. Before sealing off the cavity, smaller magnetic particles are attracted into the cavity. The sample is a magnetic particle covered with appropriate chemical(s).

In one embodiment, the arrangement includes means for detection of presence of a magnetic capping lid capping a cavity. In one embodiment, the capping is detected by detecting the change in inductance in the control circuit, which produces the attractive magnetic field whereby the bead acts like a magnetic yoke in a transformer, increasing the inductance. In another embodiment, the capping is detected through decrease of electromagnetic radiation to a detector inside the cavity or by changes of capacitance between electrodes inside the cavity or near a cavity rim.

The arrangement may also include means for detection of changes of inductance when a magnetic particle passes through the opening into or out of a cavity. The indication is determined using the direction of externally controlled magnetic field, either by changing the direction of the electric current flowing through a coil or flipping an external magnetic. Preferably, the particle contains particular molecular coating, which reacts with the liquid in that cavity or with the coating adsorbed on the walls of the cavity.

The substrate can be made of silicon, Si, or of Si-compound, such as Si-oxide Si-nitride or Si-carbide, or combinations thereof, or a suitable polymer, such as polyethylene, polyethylene glycol, polyethylene oxide, fluorine containing a polymer (PTFE BTeflon), or silicon containing a polymer.

The invention also relates to a method of preparing samples, by means of an arrangement submergible in a liquid medium. The arrangement includes a section provided with a device for generation of a magnetic field. The method includes the steps of connecting a signal to the device and generating a magnetic field to trap at least part of the samples. Each device is applied a current of different strength. The arrangement is provided by a cavity in a substrate.

According to this method, it is possible to detect the presence of a magnetic capping lid capping a cavity. The capping is determined by detecting the change in inductance in the control circuit which produces the attractive magnetic field. In this way, the bead acts like a magnetic yoke in a transformer, increasing the inductance. The capping may also be determined through decrease of electromagnetic radiation to a detector inside the cavity or by changes of capacitance between electrodes inside the cavity or near the cavity rim. According to the method, it is possible to detect changes of inductance when a magnetic particle passes through the opening into, or out of a cavity, thereby determining the indication using the direction of externally controlled magnetic field. This is accomplished either by changing the direction of the electric current flowing through a coil, or flipping an external magnetic.

According to the method, given a known number of samples in each cavity and a density of respective coatings, quantitative data on the number of reactions between the coating on a wall of the cavity and the coating on a small sample is obtained by counting the number of samples.

BRIEF DESCRIPTION OF DRAWINGS

In the following, the invention will be further described in a non-limiting way with reference to the accompanying drawings, in which.

DETAILED DESCRIPTION

A basic idea of the present invention is to create an enclosure or a crater (a well), provided with a lid, and that can be opened and closed by the "lid". A user can control the lid, and the device is intended to be submerged in a liquid medium. By operating the lid, the enclosed volume becomes separated from the surroundings. That means, the liquid stored in the crater, including particles suspended therein, and/or material that adheres to the crater's inner surface, are not affected by subsequent changes that occur in the surroundings while the lid is closed. These changes might be a different chemical composition of the liquid, light shining on the crater chip, or other solids in the surrounding liquid. The lid may or may not be completely liquid-tight, but mixing of the liquid outside a crater with the liquid contained inside a well will be dramatically slowed. Hence, solids and liquids will be well separated between inside and outside by the lid.

Figure 1:
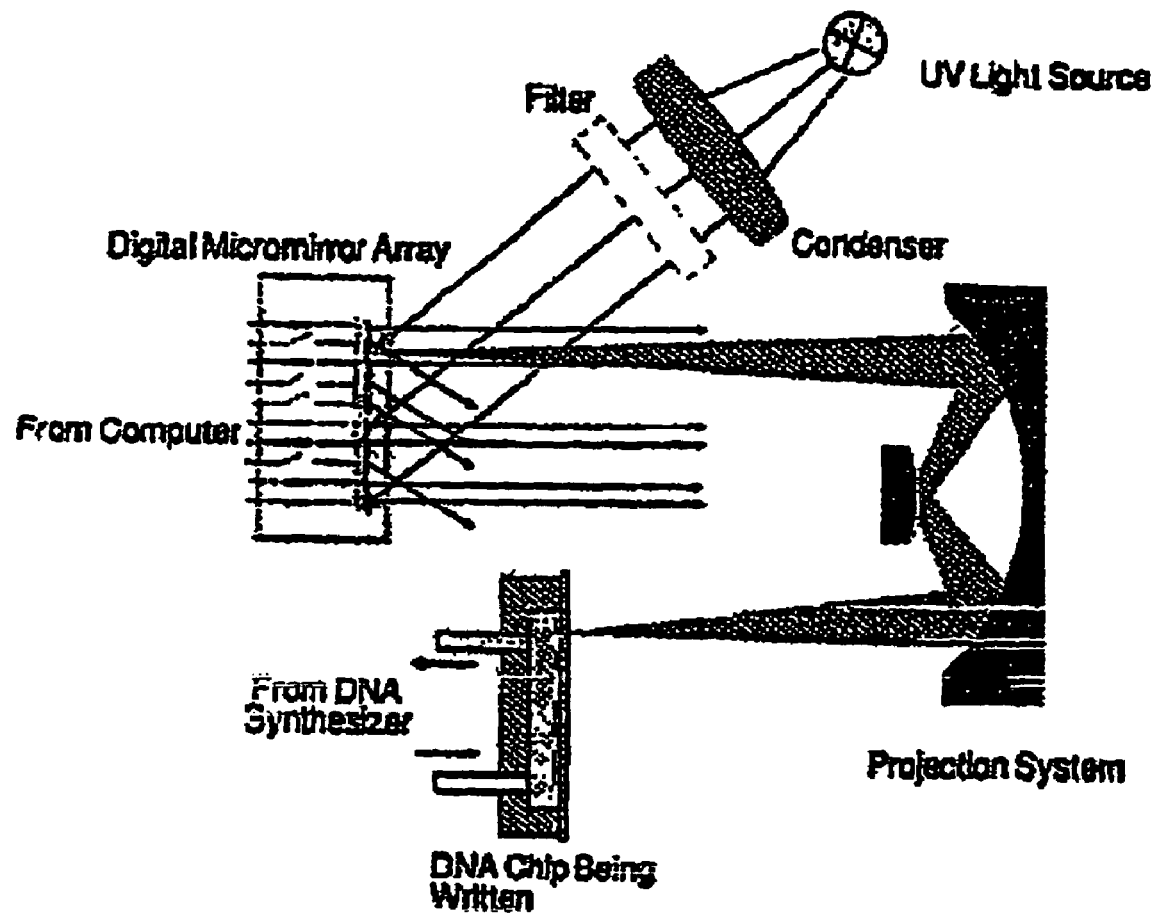
FIG. 1 shows an arrangement of conventional design.
Figure 2:
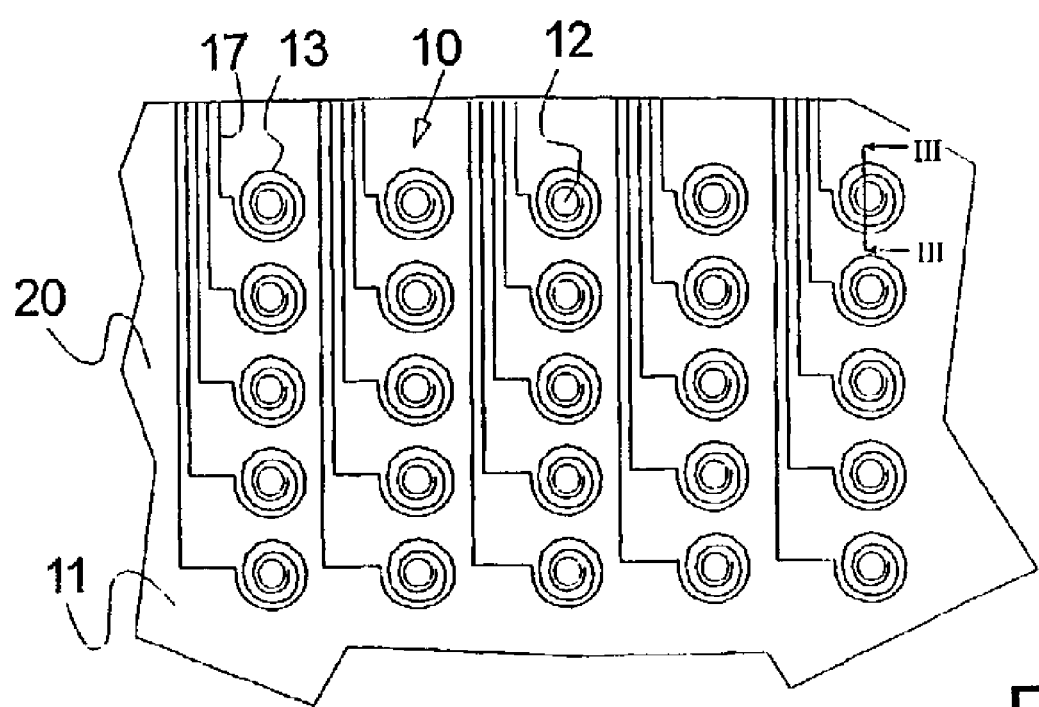
FIG. 2 is a schematic view, from above a chip according to the present invention.
Figure 3:
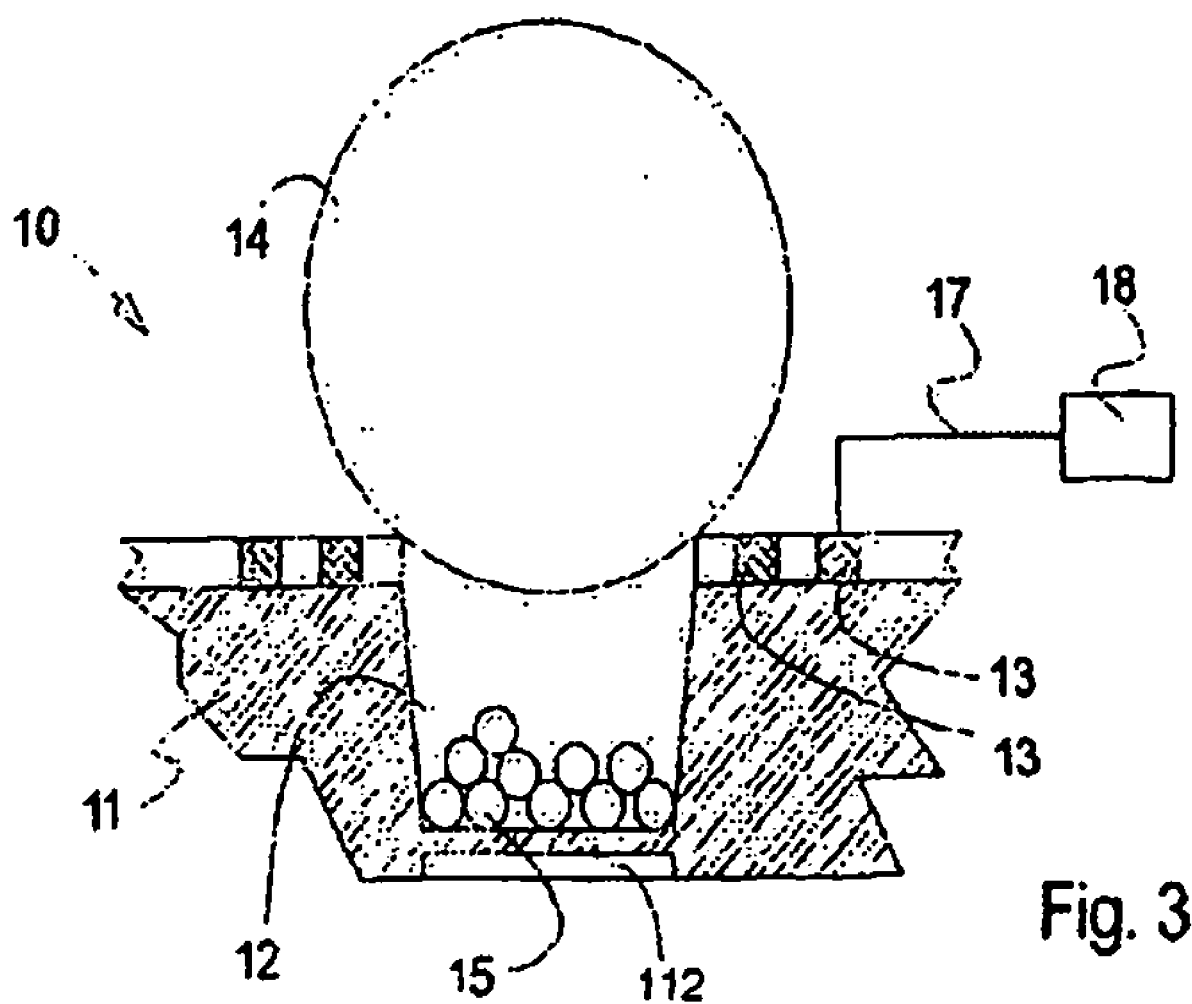
FIG. 3 is a schematic view, showing an enlarged cross-section through a part of the chip along line III-III as depicted in FIG. 2.

FIGS. 2 and 3 illustrate a preferred example of an arrangement configured according to the invention. FIG. 2 illustrates an enlarged schematic view of a part of chip 19 including a number of sample collecting arrangements 10. Each sample collecting arrangement includes a cavity (crater, pocket, or well) 12 provided in a substrate 11, and means 13 to control the cap (lid or cover) 14. Each control means 13 is connected to controller 18 (FIG. 3) through connections 17.

FIG. 3 is a schematic cross-section through the device 10. However, the device 10 is shown in a stage where samples 15 are collected and the crater 12 is closed by means of the lid or closure 14. The samples in this particular case are magnetic particles of diameter(s) much smaller than the diameter of the lid, covered with appropriate chemical(s). In this embodiment, the lid control means 13 include electrically actuated coils and the lid 14 is a magnetizeable bead.

By making many craters 12, all with individually controlled lids 14, different types of mixing of solids dispensed in a liquid and/or liquids can be achieved at the same time. As different liquids/solids are introduced to the outside of the craters, only user-selected craters with open lids will be reached for the mixing by the liquids/solids external to the closed craters.

The dimensions and the shapes of each crater 12 can of course vary within a large interval both with respect to its diameter and depth. The craters can have circular cross-section, for example being about 50 μm deep with diameters of approximately 100 μm. It is relatively easy to produce craters with dimensions ranging from a few μm and larger, and with depths ranging from a few μm and up to several hundreds of μm, in, for example, square shapes.

The material of the substrate can be silicon and the manufacturing process may include micro-machining, similar to the process of making microprocessors or memories chips. A device configured according to the invention may contain from several hundreds of craters on a single piece of silicon, establishing a so-called chip. Of course, tens of thousands of craters on commercial units can be arranged.

Preferably, the lid is a micro-bead introduced in a liquid. The lid-actuation mechanism that is used for the closing and the opening each of the craters can include using switchable magnetic fields that influence the motion of the introduced beads. The magnetic fields are created using the coils 13 deposited around each crater.

The coils 13 surrounding each of the craters are made of an electrically conducting material. In a preferred embodiment, the conductor is made of aluminum, Al, but any electrical conductor can be used. Preferably, each coil is accessible through electrically conducting leads so that a current of different strength can be applied separately to each coil. The current amplitude and the number of windings in the coil are proportional to the strength of the magnetic field, which can thus be varied. Clearly, it is possible to change the number of windings in the coils surrounding each crater as well as their width and thickness within a broad range of dimensions. Preferably, but not exclusively, coils can have from 2 to 10 windings.

In an alternative embodiment, instead of the coils 13, the control means can take the form of a magnetically active material surrounding each crater and which directs the beads using external magnets that will create magnetic fields counteracting the field created by the material deposited around each crater 12.

Preferably, the craters are etched in the silicon surface and the lid is provided by a large magnetic particle 14 in the liquid. Thus, particle 14 can be attracted to the crater of choice when the coil of this crater is energized by electric current to produce magnetic fields for spatial attraction. Before sealing off the crater of choice, however, it is also possible to attract smaller magnetic particles into the crater. To attract the smaller magnetic particles 15 to the crater, the coil is energized by an electric current. When the coil is energized, a magnetic field is established. This field will attract the magnetic particle 15 from the liquid. These smaller particles have higher mobility in the liquid compared to the mobility of larger particles and will thus reach crater faster then the larger lids. The large lid-particle will cap the crater at a later stage. Preferably, as large particles commercially available magnetic particles such as ferromagnetic or super-paramagnetic having about 100 micrometers in size can be used, while the size of the smaller particles is much smaller than the crater's size. There are other dimensions and particle types on the market and the invention is applicable a broad range of particle sizes, shapes and materials.

To open a closed crater, a repelling field is generated either externally or by inverting the direction of the current flowing through the coil. It is also possible to terminate the current through the coil, whereby the particle may be released due to shear force from the flowing liquid or due to gravitational forces if the craters are positioned "upside down."

The simple actuation of the crater lid using a current controlled magnetic field(s) and the large number of craters on a chip makes it necessary that the chip be operated automatically through a controlling arrangement. The chip is preferably provided with an interface device that establishes electrical connection with the chip and provides the handling of the surrounding fluid with the beads and chemicals. After use, the chip may be removed for cleaning and reuse or disposal. The interface device will be connected to a computer equipped with suitable software to control the sequence of operations on the craters and the liquid handling system. The software will also provide an interface for the user to establish the process sequence and to plan the states of the crater lids in each sequence.

Detection of a magnetic capping bead can also be done. It is important to obtain feedback on which craters are capped. The presence of a magnetic capping bead, in place over a crater, can be detected by the change in inductance in the electric circuit, which produces the attractive magnetic field. The bead acts like a magnetic yoke in a transformer, increasing the inductance. A resonant, or other circuit can then detect this inductance change.

The presence of the capping bead can be detected by various other schemes such as a decrease of electromagnetic radiation experienced by a detector (112) inside the crater, or by changes of capacitance between electrodes inside the crater or near the crater rim.

Another possible application along similar lines is the detection of changes of inductance when a small magnetic sphere passes through the opening into a well. Using this arrangement, according to the invention, it is possible to determine whether a sphere is entering the well, or if it is leaving the well. This is determined using the direction of an externally controlled magnetic field either by changing the direction of the electric current flowing through a coil or flipping an external magnetic field creating device by other means. Such a sphere may contain particular molecular coating, which will react with the liquid in that well or with the coating adsorbed on the walls of the crater. Given that the number of spheres is known in each well, as is the density of the respective coatings, quantitative data on the number of reactions between the coating on the wall and the coating on a small bead can be obtained by simply counting the spheres.

In the following non-limiting examples are given for simplifying the understanding of the invention. According to a first example, liquid A containing magnetic beads is introduced. User selected craters 12 are energized, and hence capped. The remaining beads are flushed away with a cleaning liquid. Now liquid B is introduced, containing small (much smaller than the capping beads) particles, called X, made of a material interesting to the user. Only uncapped craters will accept X. Then, more magnetic beads are introduced and selected craters are capped, trapping X. Cleaning liquid is used to flush all excess away. A liquid containing chemical reagent Y can then be introduced and some craters are opened. X and Y are allowed to mix and react, but only in the user-selected areas. This reaction can be followed using sensing techniques that can easily be incorporated into the system, for example using optical techniques. Other possible novel detection techniques that are easily incorporated into the present embodiment are described below.

In a second example, a substance is attached to the craters inner surface. In a repeating sequence, some craters are closed by the beads and the others are exposed to a reactive chemical A. After the reaction, the chemical is flushed and some craters are exposed to another chemical B. As a result, there will be craters that have been exposed to A and B, some to A, some to B, and some to neither. This process can be repeated with many chemicals producing very large numbers of differently modified substances residing in different locations (craters) of choice. With a sequence of 10 different chemicals, for example, more than 1000 different combinations are obtained. In particular, this could be used to synthesize DNA strands or (using appropriate well-known techniques) to investigate the function(s) of different proteins.

Yet another application of the present invention is to lock the cells in the wells filled with different chemicals and monitor the reaction of cells (cell proliferation, differentiation, spreading or others) to these chemistries. This would enable, for example, a fast, high throughput screening of drugs.

The arrangement may also be used separately, one-by-one, for example to deliver a certain chemical, or chemicals, locally at a certain place or places in a reaction vessel, and monitor reaction products locally, or to deliver a drug inside a body.

Another field of possible applications of the device has been triggered by something generally referred to as a "low throughput screening" (LTS). LTS is often used when the amount of required information is smaller, but the researcher wants to additionally obtain some quantitative information about concentrations of analyses or number of reactions that occur during certain time at certain amounts of reagents. The idea behind LTS has much in common with another timely idea often used today and referred to as an "electronic tongue." Electronic tongue is a device that enables one to determine components in a liquid. These components can then be associated with certain tastes (sweet, sour, salt, etc. or combinations thereof). To determine the content of simple liquids in a liquid mixture, for example % of sugar dissolved in a cup of tea along with the amount of tea used to prepare this cup, and even perhaps different tea blends used. To acquire knowledge about all these requires performing several experiments with constituents that react differently to different tea blends and to different amounts of tea from each blend that has been used, as well as to the amounts of sugar being dissolved in this tea. All these can be made by LTS methods using the presently disclosed equipment, and choosing appropriate reagents different for each crater and letting these first react with "standard" samples ("teaching the tongue" to recognize certain non-mixed liquids) and later exposing these samples to mixtures of different tea blends, with or without sugar. Appropriate data processing from the outcome, compared with the results obtained on standard samples, enables one often to obtain information about tea blends used and the amount of sugar dissolved.

The device is not limited to spheres or coils for creation of magnetic fields that direct beads, nor is it limited to the use of beads. Other shapes can be used. Finally, the present invention is not limited to the use of silicon technology to fabricate the crater matrices; other materials can be used for this purpose.

Additional, non-limiting examples are provide below of different crater preparation techniques, and materials of use paired with its utilization. A general concept behind these examples is to manipulate small particles in order to bring them to a chosen place on the surface of the substrate using magnetic field(s) as a driving force for particle manipulation. The surface of the substrate may or may not be patterned in a particular manner. When the substrate is patterned and the pattern consists of craters, some particles are used preferably as caps or lids to close each crater as earlier described. When the substrate is left without a pattern or patterned in a different manner (see below for an example), the particles can be used mainly as a way to enhance sensitivity of detection of the processes taking place in the device.

The magnetic force to manipulate the particles can be created using coils as described above, but it can also be created using externally applied magnets. In the former case, the field strength (and thus the magnitude of the force) is determined primarily by the number of windings in the coil and the magnitude of the electric current passed therethrough. In the latter case it is possible to control the magnitude of the magnetic force by appropriate choice of magnet position and strength.

The substrate may be made of silicon (described above), Si, or of Si-compound, e.g. Si-oxide Si-nitride or Si-carbide, or combinations thereof. It may also consist of thin self-supporting Si, or of a Si-compound, with another film of suitable thickness (for example few micrometers), such as ZnO, evaporated onto its surface. This additional film is needed if the device is to work as an acoustic wave device for detection.

The substrate may also be fabricated using other material than silicon. For example, a suitable polymer, e.g. polyethylene, polyethylene glycol, polyethylene oxide, fluorine containing a polymer (PTFE BTeflon), or silicon containing a polymer may be used as a substrate material.

When patterning, the different substrate techniques may be used depending on the substrate material and the pattern. Thus, Si and Si-compounds are suitably patterned applying techniques known from semiconductor fabrication. When patterning polymers, one can use known techniques like polymer stamping or moulding.

It is also possible to supply iron or any other magnetically active material as yoke somewhere inside the crater coil geometry to concentrate the magnetic field to that region, when a coil is activated. This can be inside, below, or around the actual crater. The idea is to build the crater coils in several layers around a crater to increase the magnetic field strength. The crater coils can be used to expel all magnetic material from inside selected craters. Magnetic material can be attracted to the inside of selected craters. Smaller magnetic particles will get attracted to the center of a coil but will sink to the bottom of the crater due to the force of gravity.

It is also possible, in advance, to prepare the floor or the walls of all the craters as a bio/chem friendly surface, while the rest of the chip surface stays inert, or vice versa. In this way, both the capping beads and the type of surface will determine where a new bio/chem substance will react or be active.

Moreover, capping beads can be used as a chemically/biologically active surface, while the rest of the chip surface is not, or vice versa. By supplying magnetic capping beads, which have been bio/chem prepared in advance, to the chip, a particular bead (surface) will be attracted to a pre-determined site. Hence, the user can, by repeatedly applying different beads and washing off unattached beads, cover the chip surface with different and well-defined surfaces. Thus, it is possible to trigger a chem./bio reaction/activity inside a crater by attracting a capping bead with the right bio/chem active surface.

The invention is not limited the shown embodiments, but can be varied in a number of ways without departing from the scope of the appended claims and the arrangement and the method can be implemented in various ways depending on application, functional units, needs and similar requirements.

The invention claimed is:

1. A sample preparing arrangement comprising:
a carrier structure;
at least one cavity in said carrier structure;
a magnetic covering structure for covering/uncovering said cavity;
a magnetic field generating element comprising an electric circuit proximal to the cavity for controllably generating a magnetic field, wherein the magnetic field regulates the positioning of the covering structure;
a control signal for regulating the magnetic field generated by the element and for regulating the covering/uncovering of the cavity; and
means for detecting the presence of the magnetic covering structure when it is covering the cavity, wherein the means for detecting the presence of the magnetic covering structure is selected from the group consisting of: a control circuit for detecting a chanae in the inductance of the electric circuit of the magnetic field generating element caused by the presence of the magnetic covering structure, an electromagnetic radiation detector inside the cavity, and a capacitance detector near the cavity.

2. The arrangement as recited in claim 1, further comprising: a magnetically active material arranged inside said cavity.

3. The arrangement as recited in claim 1, wherein said magnetic field generating element is made of an electrically conducting material.

4. The arrangement as recited in claim 1, wherein said magnetic field generating element is made of aluminum.

5. The arrangement as recited in claim 1, wherein the magnetic field is generated through a conductor, and the conductor applies currents of varying strengths to the arrangement.

6. The arrangement as recited in claim 1, wherein said magnetic field generating element comprises a coil.

7. The arrangement as recited in claim 6, wherein a current amplitude and the number of windings in the coil are proportional to the strength of the magnetic field.

8. The arrangement as recited in claim 1, wherein the cavity is provided in a substrate associated with the carrier structure.

9. The arrangement as recited in claim 1, wherein the magnetic covering structure is a magnetic capping lid for closing said cavity.

10. The arrangement as recited in claim 9, wherein said lid is a magnetic bead.

11. The arrangement as recited in 1, wherein the magnetic covering structure is a magnetic bead that is directed onto the cavity using external magnets that create magnetic fields counteracting a field created by the magnetic field generating element.

12. The arrangement as recited in claim 10, wherein said lid is a microbead introduced in a liquid medium in which the sample preparing arrangement is submerged.

13. The arrangement as recited in claim 8, wherein said cavity is etched in a silicon surface and the magnetic covering structure is provided as a large magnetic particle in a liquid medium.

14. The arrangement as recited in claim 13, wherein the the magnetic field generating element comprises a coil surrounding the cavity and wherein said particle is attracted to a predetermined cavity when the coil of said cavity is energized by electric current to produce magnetic field of spatial attraction.

15. The arrangement as recited in claim 14, wherein before sealing off the cavity, smaller magnetic particles are attracted into the cavity.

16. The arrangement as recited in claim 1, wherein said sample is a magnetic particle covered with appropriate chemical.

17. The arrangement as recited in claim 1, wherein the means for detecting the presence of the magnetic covering structure is a control circuit for detecting a change in the inductance of the electric circuit of the magnetic field generating element caused by the presence of the magnetic covering structure and wherein said capping is detected by detecting a change in inductance in said control circuit which produces an attractive magnetic field, whereby the lid acts like a magnetic yoke in a transformer, thereby increasing inductance.

18. The arrangement as recited in claim 1, wherein the means for detecting the presence of the magnetic covering structure is an electromagnetic radiation detector inside the cavity and wherein said capping is detected through decrease of electromagnetic radiation to a detector inside the cavity.

19. The arrangement as recited in claim 1, wherein the means for detecting the presence of the magnetic covering structure is a capacitance detector near the cavity and wherein said capping is detected through changes of capacitance between electrodes inside the cavity or near a cavity rim.

20. The arrangement as recited in claim 1, further comprising means for detecting changes of inductance when a magnetic particle passes through the opening into or out of the cavity.

21. The arrangement as recited in claim 20, wherein said detections are determined using the direction of externally controlled magnetic field, by one of (1) changing the direction of the electric current flowing through a coil and (2) flipping an external magnetic.

22. The arrangement as recited in claim 20, wherein said particle contains particular molecular coating, which reacts with one of (1) the liquid in that cavity and (2) with a coating adsorbed on the walls of the cavity.

23. The arrangement as recited in claim 8, wherein the substrate is made of material selected from a group of materials consisting of: silicon, Si, Si-oxide, Si-nitride, Si-carbide, polyethylene, polyethylene glycol, polyethylene oxide, fluorine containing a polymer, and silicon containing a polymer.

24. A method for preparing samples with a sample preparing arrangement, the method comprising:
 providing the sample preparing arrangement of claim 1;
 providing the control signal to the magnetic field generated by the element to cover or uncover the cavity; and
 detecting the presence or absence of the magnetic covering structure using the means for detecting.

25. The method as recited in claim 24, further comprising applying a current of varying strength to said sample preparing arrangement.

26. The method as recited in claim 24, wherein the cavity is provided in a substrate associated with the carrier structure.

27. The method as recited in claim 24, wherein said magnetic covering structure is a magnetic bead for closing said cavity.

28. The method as recited in claim 27, further comprising directing said bead onto the cavity using external magnets that create magnetic fields counteracting a field created by the magnetic field generating element.

29. The method as recited in claim 27, further comprising attracting smaller magnetic particles into the cavity before closing the cavity.

30. The method as recited in claim 29, further comprising covering said magnetic particles with a chemical.

31. The method as recited in claim 29, further comprising detection of changes of inductance when a magnetic particle passes through the opening into or out of the cavity.

32. The method as recited in claim 31, further comprising determining said changes of inductance using the direction of externally controlled magnetic field by one of (1) changing the direction of the electric current flowing through a coil and (2) flipping an external magnetic.

33. The method as recited in claim 24, wherein reactions between a wall of the cavity and a coating on the sample are quantified by counting the number of samples.

* * * * *